(12) United States Patent
Ranucci et al.

(10) Patent No.: US 10,363,030 B2
(45) Date of Patent: Jul. 30, 2019

(54) SURGICAL FASTENER

(71) Applicant: C.R. Bard, Inc., Murray Hill, NJ (US)

(72) Inventors: Kevin J. Ranucci, Warwick, RI (US); Saurav V. Gupta, Medway, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 253 days.

(21) Appl. No.: 15/246,888

(22) Filed: Aug. 25, 2016

(65) Prior Publication Data
US 2017/0027560 A1    Feb. 2, 2017

Related U.S. Application Data

(62) Division of application No. 14/075,464, filed on Nov. 8, 2013, now Pat. No. 9,445,814.

(51) Int. Cl.
*A61B 17/064* (2006.01)
*A61B 17/068* (2006.01)
(Continued)

(52) U.S. Cl.
CPC .......... *A61B 17/064* (2013.01); *A61B 17/068* (2013.01); *A61B 17/08* (2013.01);
(Continued)

(58) Field of Classification Search
CPC .......... A61B 17/068; A61B 2017/0649; A61B 17/10; A61B 17/064; A61B 2017/0647;
(Continued)

(56) References Cited

U.S. PATENT DOCUMENTS 2,407,879 A    9/1946    Haas
3,229,374 A    1/1966    Comorau
(Continued)

FOREIGN PATENT DOCUMENTS

EP    0 663 184 A1    7/1995
GB    2417208         2/2006
(Continued)

OTHER PUBLICATIONS

U.S. Appl. No. 15/587,689, filed May 5, 2017, Ranucci et al.
(Continued)

*Primary Examiner* — George J Ulsh
(74) *Attorney, Agent, or Firm* — Wolf, Greenfield & Sacks, P.C.

(57) ABSTRACT

A surgical fastener is provided for various surgical fastening applications, including attaching an implantable prosthesis, such as a soft tissue repair fabric, to tissue and/or muscle. The surgical fastener may include a coil body and a separate head that is attached to the coil body. The head may include two or more radial wings extending in an outward radial direction from the head body. Each wing may include an external thread to engage with a corresponding internal thread of a delivery device. Each wing may be spaced from an adjacent wing by an opening therebetween to receive a drive member for driving the surgical fastener. The coil body may be attached to the center of the head. A proximal-most coil of the coil body may be spaced from a distal face of the head to form a gap therebetween.

20 Claims, 3 Drawing Sheets

SECTION A-A

(51) Int. Cl.
*A61B 17/08* (2006.01)
*A61B 17/00* (2006.01)

(52) U.S. Cl.
CPC ............... *A61B 2017/00477* (2013.01); *A61B 2017/0647* (2013.01); *A61B 2017/0649* (2013.01)

(58) Field of Classification Search
CPC ........... A61B 2017/0648; F16B 1/0014; F16B 37/12; F16B 5/07; F16B 21/125
USPC .................. 606/139, 151; 411/392, 438, 411; 52/506, 512
See application file for complete search history.

(56) References Cited

U.S. PATENT DOCUMENTS

| | | | |
|---|---|---|---|
| 4,318,651 | A | 3/1982 | Ragen |
| 4,762,453 | A | 8/1988 | DeCaro |
| 4,917,554 | A | 4/1990 | Bronn |
| 5,256,133 | A | 10/1993 | Spitz |
| 5,733,307 | A | 3/1998 | Dinsdale |
| 5,904,696 | A | 5/1999 | Rosenman |
| 6,383,187 | B2 | 5/2002 | Tormala et al. |
| 6,409,445 | B1 | 6/2002 | Beale et al. |
| 7,189,251 | B2 | 3/2007 | Kay |
| 7,862,573 | B2 | 1/2011 | Darois et al. |
| 7,867,252 | B2 | 1/2011 | Criscuolo et al. |
| 8,087,142 | B2 | 1/2012 | Levin et al. |
| 8,231,639 | B2 | 7/2012 | Bolduc et al. |
| 8,292,933 | B2 | 10/2012 | Zergiebel |
| 8,343,176 | B2 | 1/2013 | Criscuolo et al. |
| 8,382,778 | B2 | 2/2013 | Criscuolo et al. |
| 9,072,511 | B2 | 7/2015 | Tegzes |
| 9,445,814 | B2 | 9/2016 | Ranucci et al. |
| 9,615,830 | B2 | 4/2017 | Ranucci et al. |
| 9,675,353 | B2 | 6/2017 | Ranucci et al. |
| 2002/0055738 | A1 | 5/2002 | Lieberman |
| 2003/0181913 | A1 | 9/2003 | Lieberman et al. |
| 2004/0193217 | A1 | 9/2004 | Lubbers et al. |
| 2005/0187568 | A1 | 8/2005 | Klenk et al. |
| 2007/0038220 | A1 | 2/2007 | Shipp |
| 2007/0088390 | A1 | 4/2007 | Paz et al. |
| 2007/0140810 | A1 | 6/2007 | Itou et al. |
| 2007/0250064 | A1 | 10/2007 | Darois et al. |
| 2008/0004626 | A1 | 1/2008 | Glazer et al. |
| 2009/0118776 | A1 | 5/2009 | Kelsch et al. |
| 2010/0010520 | A1 | 1/2010 | Takahashi et al. |
| 2010/0145393 | A1* | 6/2010 | Fallin et al. ........... A61B 17/56 606/301 |
| 2010/0256690 | A1 | 10/2010 | Appenzeller et al. |
| 2010/0274266 | A1 | 10/2010 | Rimer et al. |
| 2011/0022065 | A1 | 1/2011 | Shipp |
| 2011/0087240 | A1 | 4/2011 | Shipp |
| 2011/0092992 | A1 | 4/2011 | Darois et al. |
| 2011/0295282 | A1 | 12/2011 | Glick et al. |
| 2011/0295319 | A1 | 12/2011 | Duplessis et al. |
| 2012/0022557 | A1 | 1/2012 | Cabiri et al. |
| 2012/0101526 | A1 | 4/2012 | Bennett |
| 2013/0131700 | A1 | 5/2013 | Criscuolo et al. |
| 2013/0338706 | A1 | 12/2013 | Jimenez et al. |
| 2014/0243855 | A1 | 8/2014 | Sholev et al. |
| 2015/0133964 | A1 | 5/2015 | Ranucci et al. |
| 2015/0133970 | A1 | 5/2015 | Ranucci et al. |
| 2015/0133971 | A1 | 5/2015 | Ranucci et al. |
| 2015/0133972 | A1 | 5/2015 | Ranucci et al. |
| 2015/0152908 | A1 | 6/2015 | Schwarzbich |
| 2017/0143340 | A1 | 5/2017 | Ranucci et al. |
| 2017/0231632 | A1 | 5/2017 | Ranucci et al. |

FOREIGN PATENT DOCUMENTS

| | | |
|---|---|---|
| WO | WO 1997/07744 A1 | 3/1997 |
| WO | WO 2002/09625 A1 | 2/2002 |
| WO | WO 2005/004727 A1 | 1/2005 |
| WO | WO 2005/081936 A2 | 9/2005 |
| WO | WO 2011/092692 A2 | 8/2011 |
| WO | WO 2012/176195 A2 | 12/2012 |
| WO | WO 2013/046115 A1 | 4/2013 |

OTHER PUBLICATIONS

U.S. Appl. No. 15/402,955, filed Jan. 10, 2017, Ranucci et al.
U.S. Appl. No. 14/075,354, filed Nov. 8, 2013, Ranucci et al.
[No Author Listed], Winding. (n.d.). Dictionary.com Unabridged. Retrieved Apr. 14, 2016 from Dictionary.com website. 12 Pages. http://www.dictionary.com/browse/winding.

* cited by examiner

SECTION A-A

SURGICAL FASTENER

RELATED APPLICATIONS

This Application claims the benefit under 35 U.S.C. § 120 and is a divisional of U.S. application Ser. No. 14/075,464, entitled "SURGICAL FASTENER" filed on Nov. 8, 2013, which is herein incorporated by reference in its entirety.

FIELD

Disclosed embodiments are related to a surgical fastener, and more particularly, to a surgical fastener that includes a coil body with an attached head.

BACKGROUND

Surgical fasteners are widely used in many different medical procedures. For example, staples, sutures, clips and other fasteners are commonly used in laparoscopic and open surgical procedures.

SUMMARY

In one aspect of the invention, a surgical fastener comprises a head and a coil body that is separate from and attached to the head. The head includes a head body and at least two radial wings extending in an outward radial direction from the head body. Each wing includes at least one external thread to engage with a corresponding internal thread of a delivery device. Each wing is spaced from an adjacent wing by an opening therebetween that is adapted to receive a drive member for driving the surgical fastener. The coil body includes a plurality of coil windings and has a proximal end and a distal end. The proximal end is attached to the head.

In another aspect of the invention, a surgical fastener comprises a head and a coil body that is separate from and attached to the head. The head includes at least one external thread to engage with a corresponding internal thread of a delivery device. The coil body includes a plurality of coil windings and has a proximal end and a distal end. The proximal end is attached to the center of the head.

In yet another aspect of the invention, a method includes: rotating a head of a surgical fastener in a distal end of a deployment instrument, wherein the head includes a head body and at least two radial wings extending in an outward radial direction from the head body, each wing including at least one external thread engaged with a corresponding internal thread at the distal end of the deployment instrument, each wing being spaced from an adjacent wing by an opening therebetween, and wherein the surgical fastener includes a coil body that is separate from and attached to the head, the coil body including a plurality of coil windings, the coil body having a proximal end and a distal end, the proximal end being attached to the head; and deploying the surgical fastener out of the deployment instrument.

BRIEF DESCRIPTION OF DRAWINGS

Various embodiments of the invention will now be described, by way of example, with reference to the accompanying drawings, in which.

DETAILED DESCRIPTION OF INVENTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

A surgical fastener is provided for various surgical fastening applications. For example, the surgical fastener may be used to attach an implantable prosthesis, such as a soft tissue repair fabric, to tissue and/or muscle. Other non-limiting applications for the fastener may involve joining portions of tissue and/or muscle together, joining portions of tissue and/or muscle to bone, and/or joining an implantable prosthesis to bone.

In one embodiment, the surgical fastener may include a coil body and a separate head that is attached to the coil body. This arrangement may improve the manufacturability of the fastener and reduce costs, particularly as compared to costs associated with injection molding a complex surgical fastener. This arrangement may be particularly suited for manufacturing the head and coil body from different materials.

Figure 2:
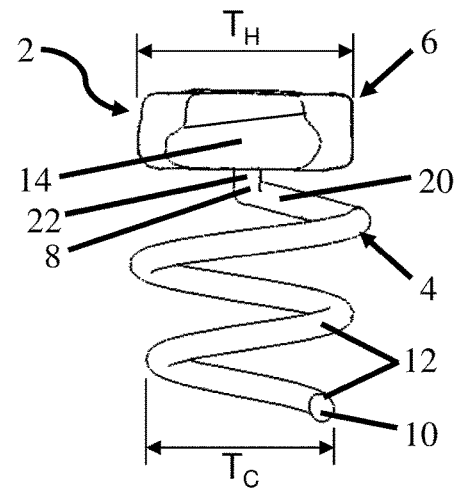
FIG. 2 is a schematic side view of the surgical fastener of FIG. 1.

For the purposes of this application, a transverse dimension of the coil body or head generally refers to a dimension of the coil body or head within a plane that is perpendicular to a long axis of the surgical fastener when it is assembled (e.g. a diameter of a cylindrical coil body, a width of a rectangular head, the length of a side of a triangular coil body, etc. . . . ). For example, an outer transverse dimension of the coil body would refer to the lateral distance between opposing outer surfaces of the coil body and an inner transverse dimension of the coil body would refer to the lateral distance between opposing interior surfaces of the coil body. The outer transverse dimensions of the head $T_H$ and coil body $T_C$ in one embodiment are illustrated in FIG. 2 and correspond to the width of the head and the diameter of the coil body. It should be noted that in embodiments in which the head and/or the coil body are noncircular, the head and/or coil body may have both minimum and maximum transverse dimensions.

In one embodiment, the head may be configured to be larger, such as wider or greater in diameter, than a transverse dimension of the coil body to engage and secure underlying material and/or tissue. Additionally, the head may include one or more features that cooperate with corresponding features of a delivery device for driving the fastener from the device and into an implantable prosthesis and/or tissue or muscle.

Depending on the embodiment, the head may include two or more radial wings extending in an outward radial direction from a head body. Each wing may include an external thread to engage with a corresponding internal thread of a delivery device. Each wing may also be spaced from an adjacent wing by an opening, such as a slot, positioned therebetween and adapted to receive a drive member for driving the surgical fastener. The coil body may have a smaller maximum outer transverse dimension than the wings so that the coil windings do not interact with the internal thread of the delivery device when the external threads of the wings engage the internal thread. The coil body may also have a smaller maximum outer transverse dimension than the head body so that the coils do not interfere with the drive member received within the slots. The head may also include one or more openings for supporting tissue ingrowth thereto.

In some embodiments, the coil body may be attached to the center of the head. In such an embodiment, a proximal-most coil winding of the coil body may be spaced from a distal face of the head to form a gap therebetween. The coil body may also include a central post at the proximal end that is attached to the center of the head. The central post may be shaped to facilitate retention of the head. For example, the central post may have an axial portion and a radial portion that extends from a proximal end of the axial portion to aid in attaching and retaining the central post relative to the head.

In one illustrative embodiment shown in FIGS. 1-5, the surgical fastener 2 may include a coil body 4 and a separately manufactured head 6 that is attached to a proximal end of the coil body 8. The distal end of the coil body 10 may be configured for penetrating an implantable prosthesis, tissue, muscle, and/or bone. In one embodiment, the distal end 10 may include a sharp distal tip, although the distal end may employ any suitable configuration as should be appreciated by one of skill.

Figure 1:
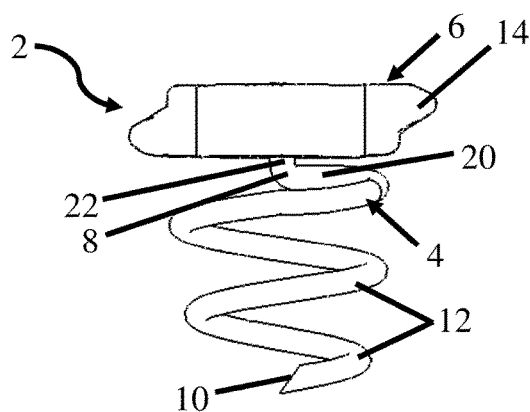
FIG. 1 is a schematic front view of a surgical fastener.

The coil body 4 includes a plurality of coil windings 12. As illustrated, the coil windings 12 may be arranged in a helical or spiral configuration suitable for driving the fastener into and through prosthetic material, tissue, muscle and/or bone. Thus, the coil body may be cylindrical in shape with a circular cross-section, though other cross-sectional shapes such as triangular, rectangular, or any other appropriate shape also are contemplated. The coil body 4 may include any number of coil windings 12 with any desired spacing or pitch between the adjacent coil windings and any diameter, or other appropriate transverse dimension, including outer, inner and pitch diameters, suitable for a particular application as should be appreciated by one of skill. In one embodiment, the coil body 4 may include coil windings 12 having the same transverse dimension. However, if desired, one or more of the coil windings may have different transverse dimensions relative to each other. For example, the coil body may employ coil windings 12 that decrease in transverse dimension from the proximal end toward the distal end to form a coil body 4 with a conical or tapered shape as illustrated in FIGS. 1 and 2.

It should be understood that the head may have any suitable configuration desired for a particular application. For example, in one embodiment, the head includes, but is not limited to, a generally flat distal face from which extends the coil body. The opposite or proximal face of the head may have one or more generally flat, round, angled or beveled surfaces, or combinations thereof, as should be apparent to one of skill.

In one illustrative embodiment, and as shown in FIGS. 1-10, the head can include at least two radial wings 14 extending in an outward radial direction from the head body 16. Each wing 14 may include one or more external threads to engage with a corresponding internal thread of a delivery device. The wings 14 may extend radially outwards by an appropriate distance such that they have a maximum outer transverse dimension that is larger than a maximum outer transverse dimension of the coil body. In such an arrangement, the coil windings may not interact with the internal thread of the delivery device when the external threads of the wings 14 engage the internal thread. It is to be appreciated that the wings may employ any suitable configuration that should be apparent to one of skill in the art.

To facilitate rotation of the fastener, the head 6 may include one or more drive features that may be engaged by a drive member of a delivery device to rotate the head, and thereby rotate the fastener including the coil body 4. In one embodiment, each wing 14 may be spaced from an adjacent wing 14 by an opening 18, such as a slot, therebetween that is adapted to receive a drive member for driving the surgical fastener, see FIG. 8. The coil body 4 may have a transverse dimension that is smaller than the head body 16 so that the coils do not interfere with the drive member received within the slots. It is to be appreciated that the head 6 may include any number of drive features having any suitable configuration as should be apparent to one of skill.

Again referring to FIGS. 1-5, in one illustrative embodiment, the coil body 4 may be attached to the center of the head 6. This arrangement may permit maximum use of the entire length of the coil body 4 by permitting over-compression or over-driving of the surgical fastener head 6 into an underlying prosthetic material and/or tissue while reducing, if not eliminating, the potential for ripping or tearing of the material and/or tissue as compared to a fastener in which the coil body terminates closer to the outer periphery of the head 6. Without wishing to be bound by theory, this may be due to the reduced moment arm, and thus reduced torque, present at the center of the head as it is rotated. However, it is to be appreciated that it is not required for the coil body 4 to be attached directly at the center of the head 6 in each embodiment of the surgical fastener and that other attachment configurations may be used as should be apparent to one of skill. For example, the coil body 4 might be attached to the head 6 at any desirable point between the center of the head and the outer perimeter of the head.

It may also be desirable to reduce, if not eliminate, the potential for pinching a prosthetic material and/or tissue between the coil body and the head. In one illustrative embodiment as also shown in FIGS. 1-5, the proximal end of the coil body 8 may be attached to the head 6 with a proximal-most coil winding 20 being spaced from the head to form a gap therebetween. This arrangement may be implemented in place of or together with the center attachment described above. In one embodiment, the fastener may employ a gap of approximately 0.002 inches to approximately 0.005 inches (0.05 mm to 0.13 mm), although a gap of any suitable size may be employed as should be apparent to one of skill. However, it is to be appreciated that a gap between the coil body 4 and the head 6 is not required for each embodiment of the surgical fastener.

Figure 10:
FIG. 10 is a schematic cross-sectional view of the surgical fastener head of FIG. 6.
Figure 11:
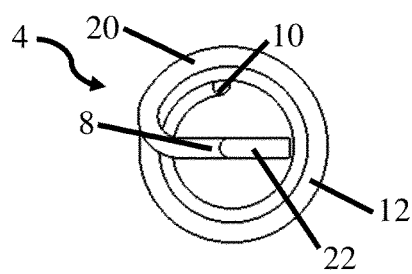
FIG. 11 is a schematic top view of a surgical fastener coil body.
Figure 12:
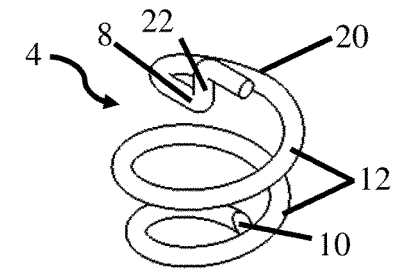
FIG. 12 is a schematic perspective view of the surgical fastener coil body of FIG. 11.
Figure 13:
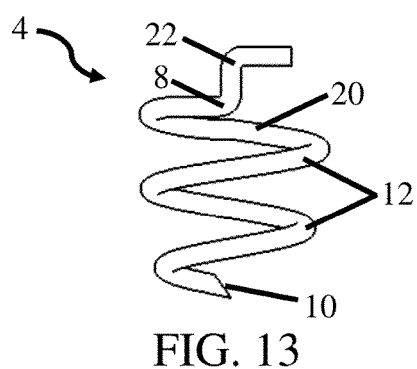
FIG. 13 is a schematic front view of the surgical fastener coil body of FIG. 11.
Figure 14:
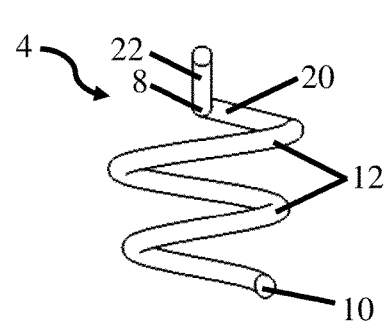
FIG. 14 is a schematic side view of the surgical fastener coil body of FIG. 11.

Depending on the embodiment, the head may be attached to the coil body by molding, or otherwise attaching, a non-winding feature of the coil body 8 and head 6 together. For example, the head may be molded to a prefabricated coil body using an insert molding or over-molding process as should be apparent to one of skill. In one illustrative embodiment shown in FIGS. 10-14, the coil body 4 may include a non-winding feature such as a central post 22 at the proximal end 8 that is attached to the head, such as by molding. A corresponding cavity 24 is formed in the head 6 during molding to accommodate and retain the central post 22 is illustrated in FIG. 10. The central post 22 may include an axial portion and a radial portion that extends from a proximal end of the axial portion. The radial portion may be oriented so as to extend in a direction toward one of the wings to maximize its length for enhanced holding between the head and the coil body, though other directions are also possible. Without wishing to be bound by theory, employing a longer radial portion may increase the amount of torque that may be applied to the coil body through the head due to the increased area the torque is applied to and the increased attachment strength. While a particular non-winding feature for attaching the coil body to the head is describe above, any suitable arrangement may be employed to attach the coil body to the head as should be apparent to one of skill.

Figure 3:
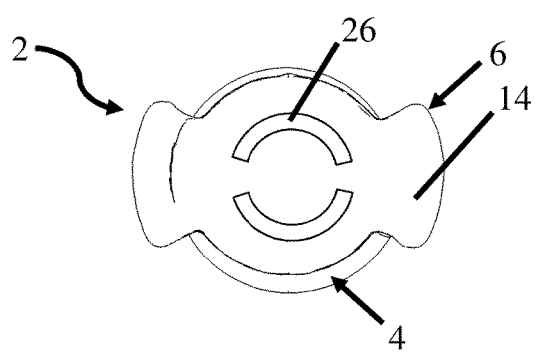
FIG. 3 is a schematic top view of the surgical fastener of FIG. 1.
Figure 4:
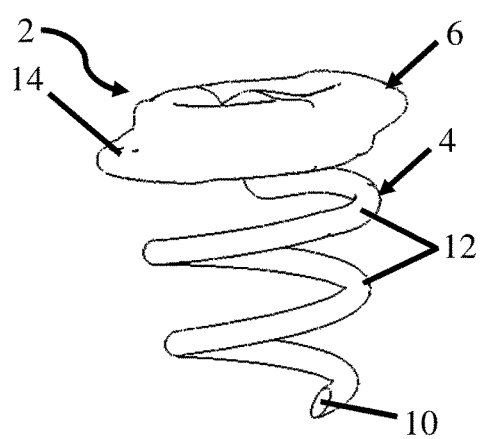
FIG. 4 is a schematic perspective view of the surgical fastener of FIG. 1.
Figure 5:
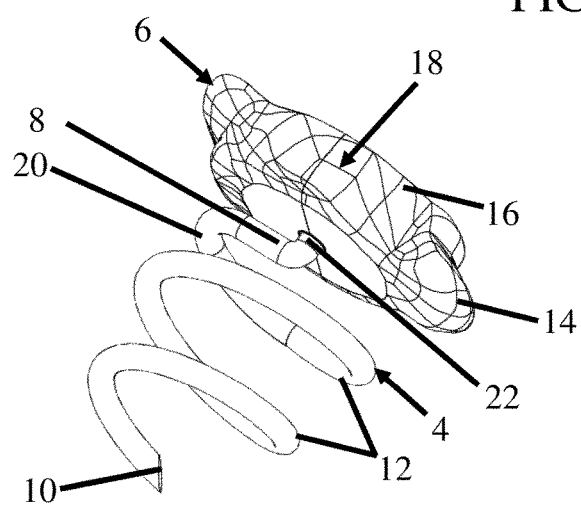
FIG. 5 is a schematic perspective view of the surgical fastener of FIG. 1.
Figure 6:
FIG. 6 is a schematic front view of a surgical fastener head.
Figure 7:
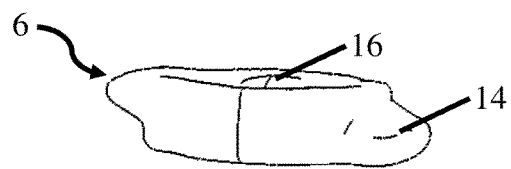
FIG. 7 is a schematic perspective view of the surgical fastener head of FIG. 6.
Figure 8:
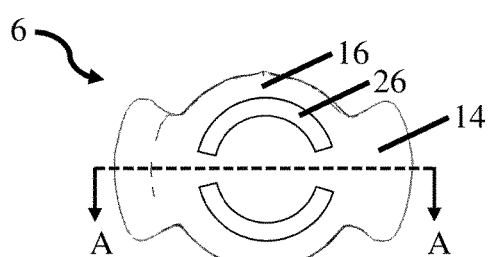
FIG. 8 is a schematic top view of the surgical fastener head of FIG. 6.
Figure 9:
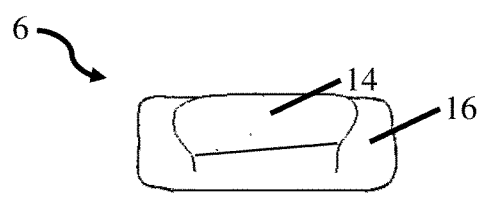
FIG. 9 is a schematic side view of the surgical fastener head of FIG. 6.

The surgical fastener may be configured to reduce, if not prevent, post-operative back out of the fastener. In one illustrative embodiment as best shown in FIGS. 3 and 8, the head 6 may include one or more features 26 that permit tissue ingrowth into or through the head to help anchor the head in position. In one embodiment, the head 6 may include features 26 for tissue ingrowth such as one or more openings, holes, recesses, cavities, slots and the like that are configured to permit ingrowth into and/or through the head 6 as should be apparent to one of skill in the art. However, it is to be appreciated that such ingrowth features are not required for each embodiment of the surgical fastener. Additionally, in some embodiments features 26 may be used as driving features that engage with suitably shaped and arranged guide rods to drive the surgical fastener. In such an embodiment, the surgical fasteners may not include the wings and associated slots described above, and instead may include a circular threaded head that engages a corresponding internal thread of a delivery device.

In one embodiment, the surgical fastener may include a coil body having a length of approximately 3 mm (0.118 inches) to approximately 5.5 mm (0.217 inches) extending from the distal face of the head. The coil body may include approximately 2.5 turns to approximately 6 turns of coils having a maximum outer transverse dimension of approximately 2.5 mm (0.100 inches) to approximately 4.9 mm (0.193 inches), for delivery through a 5 mm cannula, with a pitch of approximately 0.7 mm (0.03 inches) to approximately 1.1 mm (0.045 inches). The head may include wings with an external thread that corresponds to the internal thread of a delivery device. The head body may have a maximum outer transverse dimension of approximately 4 mm (0.157 inches) to approximately 4.9 mm (0.193 inches) at the slots and a thickness of approximately 0.97 mm (0.030 inches) to approximately 1.02 mm (0.04 inches). The head may have a thickness of approximately 0.97 mm (0.030 inches) to approximately 1.02 mm (0.04 inches). The radial portion of the center post may have a length of approximately 3.05 mm (0.12 inches) to approximately 3.30 mm (0.13 inches) and may be located about midway between the proximal and distal faces of the head. Of course, the surgical fastener may employ a coil body and head having any suitable sizes and configurations for a desired application as should be apparent to one of skill in the art.

The surgical fastener may be made from one or more biocompatible materials that are suitable for a particular surgical application and is sterilized or sterilizable. The components of the fastener may be made from a non-absorbable material, an absorbable material or a combination of absorbable and non-absorbable materials. The components may be made from, and/or coated with, materials and/or include features that may resist tissue ingrowth and/or adhesions, permit tissue ingrowth and/or adhesions, or a combination thereof. The components may be made from metal, plastic and/or any other suitable materials as should be apparent to one of skill in the art.

In one embodiment, the head may be made from a plastic polymer including, but not limited to, polyether ether ketone (PEEK) or acetal, and the coil body may be made from a metal including, but not limited to, stainless steel, nitinol, or titanium. If desired, the head alone or the head and the coil body may be made from an absorbable material metal and/or polymer. Other materials for both the head and coil body are possible.

In one exemplary embodiment, the surgical fastener may has an overall length of approximately 4.5 mm (0.177 inches) with a coil length extending from the head of approximately 3.5 mm (0.138 inches). The head has a thickness of approximately 1 mm and an outer transverse dimension of approximately 4 mm (0.157 inches) to 4.25 mm (0.167 inches) at the slots. The coil body has an outer transverse dimension of approximately 2.7 mm (0.105 inches) and is formed of 0.46 mm (0.018 inch) metal wire to have a constant pitch of approximately 0.91 mm (0.036 inches) to 1.07 mm (0.042 inches).

Figure 15:
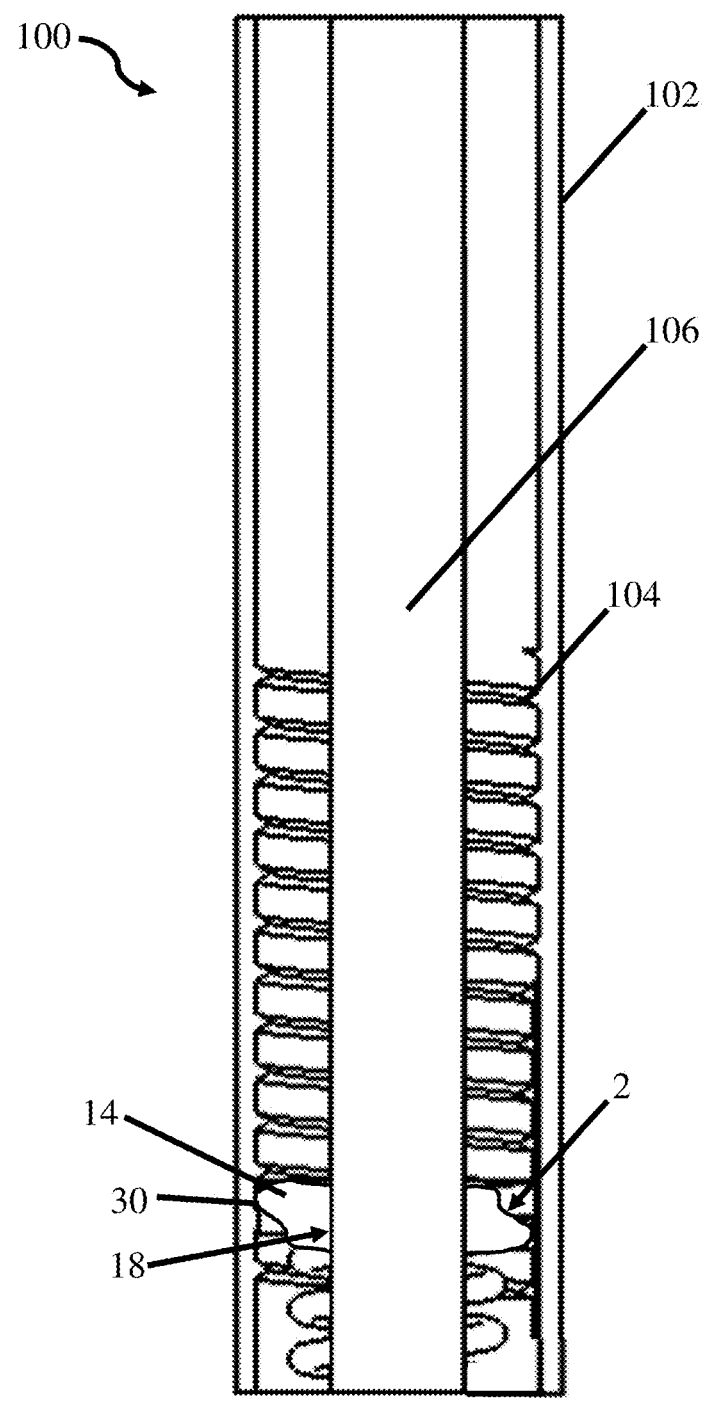
FIG. 15 is a schematic cross-sectional view of a delivery device.

The surgical fastener may be delivered to a surgical site using a delivery device that imparts rotation to the fastener and drives the fastener into prosthetic material, tissue, muscle and/or bone. As shown in FIG. 15, the delivery device 100 may include an outer tube or cannula 102 for supporting and/or guiding one or more fasteners 2 within the cannula. The outer tube 102 may include an internal thread 104 that corresponds to and engages the external thread 30 of the head located on wings 14. One or more drive members 106 may extend along the length of the outer tube 102 and mate with the slots 18 of each fastener. The drive members 106 may be rotated about the longitudinal axis of the outer tube to rotate the head of the fastener and thereby rotate each fastener 2 within the outer tube 102. Rotation of the head 6 relative to the internal thread 104 of the outer tube 102 in turn provides a reactive thrust to the fastener causing the fastener to be driven in a distal direction along the length of the drive members 106, out of the outer tube 102 and into the prosthetic material, bone, muscle and/or tissue. However, it is to be appreciated that the surgical fastener may be delivered using other suitable arrangements and delivery devices as should be apparent to one of skill in the art. For example, the surgical fasteners could be used in delivery devices such as a laparoscopic device, an endoscopic device, a borescopic device, a catheter, a surgical instrument for use in "open" procedures, or any other appropriate surgical instrument.

It should be understood that the foregoing description of various aspects of at least one embodiment of the invention are intended merely to be illustrative thereof and that other embodiments, modifications, and equivalents of the invention are within the scope of the invention recited in the claims appended hereto. Accordingly, the foregoing description and drawings are by way of example only.

What is claimed is:

1. A method comprising:
rotating a head of a surgical fastener in a distal portion of a deployment instrument, wherein the surgical fastener includes a coil body that is separately formed from and attached to the head, the coil body including a plurality of coil windings, the coil body having a proximal end and a distal end, the proximal end being attached to the head, wherein at least one external thread of the head is engaged with an internal thread of the deployment device, and wherein rotating the head transmits a torque to a proximal end of the coil body attached to a center portion of the head; and
deploying the surgical fastener out of the deployment instrument.

2. The method of claim 1, further comprising driving the surgical fastener in a distal direction and into tissue, muscle, bone, and/or a prosthesis.

3. The method of claim 2, wherein driving the surgical fastener comprises the internal thread of the delivery device applying a distally directed force to the at least one external thread as the head is rotated.

4. The method of claim 1, wherein the head includes a head body and at least two radial wings extending in an outward radial direction from the head body, wherein the at least one external thread of the head includes at least one external thread formed on each wing that engages the internal thread of the deployment instrument to drive the surgical fastener in the distal direction, and wherein each wing is spaced from an adjacent wing by an opening therebetween.

5. The method of claim 4, wherein a maximum outer transverse dimension of the coil body is smaller than a maximum outer transverse dimension of the wings so that the coil body does not interact with the internal thread of the delivery device when the external threads of the wings engage the internal threads.

6. The method of claim 1, further comprising maintaining a gap between a proximal-most coil winding and the head.

7. The method of claim 6, wherein the gap is between 0.05 mm and 0.13 mm inclusively.

8. The method of claim 1, wherein rotating the head transmits the torque to the proximal end of the coil body using a central post located at the proximal end of the coil body that is attached to the center portion of the head.

9. The method of claim 4, wherein the head body is constructed and arranged to support tissue ingrowth.

10. The method of claim 9, wherein the head body includes one or more openings adapted to receive tissue ingrowth.

11. The method of claim 1, wherein the head and the coil body are fabricated from different materials.

12. The method of claim 11, wherein the head comprises a plastic or metal material.

13. The method of claim 12, wherein the coil body comprises a plastic or metal material.

14. The method of claim 1, wherein the coil body extends between 3 mm to 5.5 mm inclusively from a distal face of the head.

15. The method of claim 1, wherein a maximum outer transverse dimension of the coil body is between 2.5 mm to 4.9 mm inclusively.

16. The method of claim 1, wherein a maximum outer transverse dimension of the head is between 4 mm to 4.9 mm inclusively.

17. The method of claim 1, wherein the coil body includes interior opposing surfaces on opposite sides of a long axis of the surgical fastener.

18. The method of claim 1, wherein a portion of the separately formed coil body extends into the head.

19. A method comprising:
rotating a head of a surgical fastener in a distal portion of a deployment instrument, wherein the surgical fastener includes a coil body that is separate from and attached to the head, the coil body including a plurality of coil windings, the coil body having a proximal end and a distal end, the proximal end being attached to the head, wherein at least one external thread of the head is engaged with an internal thread of the deployment device, and wherein rotating the head transmits a torque to a proximal end of the coil body attached to a center portion of the head; and
deploying the surgical fastener out of the deployment instrument, wherein rotating the head transmits the torque to the proximal end of the coil body using a central post located at the proximal end of the coil body that is attached to the center portion of the head wherein the central post includes an axial portion and an elongated radial portion that extends from a proximal end of the axial portion; and wherein the axial portion extends in a first direction and the elongated radial portion extends in a second direction that is different from the first direction.

20. The method of claim 19, wherein rotating the head transmits the torque to the proximal end of the coil body using both an axial portion and a radial portion of the coil body.

* * * * *